United States Patent [19]
Hemmings

[11] Patent Number: 6,159,704
[45] Date of Patent: Dec. 12, 2000

[54] PHOSPHATASE MODULATOR

[75] Inventor: Brian Arthur Hemmings, Bettingen, Switzerland

[73] Assignee: Novartis AG, Basel, Switzerland

[21] Appl. No.: 09/155,427

[22] PCT Filed: Mar. 17, 1997

[86] PCT No.: PCT/EP97/01330

§ 371 Date: Sep. 28, 1998

§ 102(e) Date: Sep. 28, 1998

[87] PCT Pub. No.: WO97/37037

PCT Pub. Date: Oct. 9, 1997

[30] Foreign Application Priority Data

Mar. 29, 1996 [GB] United Kingdom .................. 9606707
Dec. 20, 1996 [GB] United Kingdom .................. 9626470

[51] Int. Cl.[7] .............................. C12Q 1/42; C12Q 1/68; C12N 9/16
[52] U.S. Cl. .................. 435/21; 435/6; 435/196
[58] Field of Search .................. 435/196, 195, 435/18, 4, 6, 21

[56] References Cited

U.S. PATENT DOCUMENTS 5,180,665   1/1993   Holmes ..................................... 435/21

FOREIGN PATENT DOCUMENTS

| | | |
|---|---|---|
| 0 551 200 | 7/1993 | European Pat. Off. . |
| WO 92 09891 | 11/1992 | WIPO . |
| WO 97/37224 | 10/1997 | WIPO . |
| WO 98/14606 | 4/1998 | WIPO . |
| WO 98/24915 | 6/1998 | WIPO . |

OTHER PUBLICATIONS

Quigley et al. (Sep. 23, 1993) EMBL database Accession No. Z26378.
Quigley et al. (Sep. 23, 1993) EMBL database Accession No. Z26379.
Quigley et al. (Sep. 23, 1993) EMBL database Accession No. Z26380.
Quigley et al. (Sep. 23, 1993) EMBL database Accession No. Z26381.
Quigley et al. (Sep. 23, 1993) EMBL database Accession No. Z26382.
Quigley et al. (Sep. 23, 1993) EMBL database Accession No. Z26383.
Quigley et al. (Sep. 23, 1993) EMBL database Accession No. Z26384.
Quigley et al. (Sep. 23, 1993) EMBL database Accession No. Z26385.
Quigley et al. (Sep. 23, 1993) EMBL database Accession No. Z26386.
Quigley et al. (Sep. 23, 1993) EMBL database Accession No. Z26387.
Quigley et al. (Sep. 23, 1993) EMBL database Accession No. Z26388.
Quigley et al. (Sep. 23, 1993) EMBL database Accession No. Z26389.
Quigley et al. (Sep. 23, 1993) EMBL database Accession No. Z26390.
Quigley et al. (Sep. 23, 1993) EMBL database Accession No. Z26391.
Quigley et al. (Sep. 23, 1993) EMBL database Accession No. Z26392.
Quigley et al. (Sep. 23, 1993) EMBL database Accession No. Z26393.
Quigley et al. (Sep. 23, 1993) EMBL database Accession No. Z26394.
Quigley et al. (Sep. 23, 1993) EMBL database Accession No. Z26395.
Quigley et al. (Sep. 23, 1993) EMBL database Accession No. Z26396.
Quigley et al. (Oct. 6, 1993) EMBL database Accession No. Z26658.
Quigley et al. (Oct. 6, 1993) EMBL database Accession No. Z26659.
Quigley et al. (Oct. 6, 1993) EMBL database Accession No. Z26660.
Quigley et al. (Oct. 6, 1993) EMBL database Accession No. Z26661.
Quigley et al. (Oct. 6, 1993) EMBL database Accession No. Z26662.
Quigley et al. (Oct. 6, 1993) EMBL database Accession No. Z26663.
Quigley et al. (Oct. 6, 1993) EMBL database Accession No. Z26664.
Quigley et al. (Oct. 6, 1993) EMBL database Accession No. Z26665.
Quigley et al. (Oct. 6, 1993) EMBL database Accession No. Z26656.
Quigley et al. (Oct. 6, 1993) EMBL database Accession No. Z26667.
Quigley et al. (Oct. 6, 1993) EMBL database Accession No. Z26668.
Quigley et al. (Oct. 6, 1993) EMBL database Accession No. Z26669.
Quigley et al. (Oct. 6, 1993) EMBL database Accession No. Z26670.
Quigley et al. (Oct. 6, 1993) EMBL database Accession No. Z26671.
Quigley et al. (Oct. 6, 1993) EMBL database Accession No. Z26672.
Quigley et al. (Oct. 6, 1993) EMBL database Accession No. Z26673.
Quigley et al. (Oct. 6, 1993) EMBL database Accession No. Z26674.

(List continued on next page.)

*Primary Examiner*—Elizabeth Slobodyansky
*Attorney, Agent, or Firm*—Michael U. Lee; Myra H. McCormack

[57] ABSTRACT

The interaction between PP2Ac and eRF1 is described. The invention provides a method for identifying modulators of protein expression comprising screening for agents which affect the interaction between PP2A and eRF1, screening systems incorporating methods according to the invention and modulators of protein synthesis which target the eRF1-PP2A interaction.

4 Claims, No Drawings

OTHER PUBLICATIONS

Quigley et al. (Oct. 6, 1993) EMBL database Accession No. Z26675.

Andjelkovic et al. EMBO Journal, vol. 15, No. 24, "The catalytic subunit of protein phosphatase 2A associates with the translation termination factor eRF1", pp. 7156–7167 (1996).

Breining et al., Nucleic Acids Research, vol. 14, No. 13, pp. 5187–5197 (1986).

Feinberg et al., Analytical Biochemistry, vol. 132, "A Technique for Radiolabeling DNA Restriction Endonuclease Fragments to High Specific Activity[1]", pp. 6–13 (1983).

Fields et al., Nature, vol. 340, "A novel genetic system to detect protein—protein interactions", pp. 245–246 (1989).

Frolova et al., Nature vol. 372, "A highly conserved eukaryotic protein family possessing properties of polypeptide chain relase factor" pp. 701–703, 1994.

Healy et al., Molecular and Cellular Biology, vol. 11, No. 11, "CDC55, a *Saccharomyces cerevisiae* Gene Involved in Cellular Morphogenesis: Identification, Characterization, and Homology to the B Subunit of Mammalian Type 2A Protein Phosphatase", pp. 5767–5780 (1991).

Hemmings et al., Biochemistry 1990, vol. 29, "α– and β–Forms of the 65–kDA Subunit of Protein Phosphatase 2A Have a Similar 39 Amino Acid Repeating Structure", pp. 3166–3173 (1990).

Hendrix et al. Journal of Biological Chemistry, vol. 268, No. 10, "Analysis of subunit Isoforms in Protein Phosphatase 2A Holoenzymes from Rabbit and Xenopus", pp. 7330–7337 (1993).

Hendrix et al., Journal of Biological Chemistry, vol. 268, No. 20, "Structure and Expression of a 72–kDa Regulatory subunit of Protein Phosphatase 2A", pp. 15267–15276 (1993).

Hubbard et al., Trends Biochem Sci., vol. 18, "On target with a new mechanism for the regulation of protein phosphorylation", pp. 172–177 (1993).

Khew–Goodall et al., Biochemistry, vol. 30, "Structure and Transcriptional Regulation of Protein Phosphatase 2A Catalytic Subunit Genes", pp. 89–97 (1991).

Mayer–Jaekel et al., Trends in Cell Biology, vol. 4, "Protein phosphatase 2A—a 'ménage à trois'" pp. 287–291 (1994).

Mayer er al., Biochemistry, vol. 30, No. 15, "Structure of the 55–kDa Regulatory Subunit of Protein Phosphatase 2A: Evidence for a Neuronal–Specific Isoform", pp. 3589–3597 (1991).

Mumby et al., Physiological Reviews, vol. 73, No. 4, "Protein Serine/Threonine Phosphatases: Structure, Regulation, and Functions in Cell Growth", pp. 673–699 (1993).

Shacter, Analytical Biochemistry, vol. 138, Organic Extraction of $P_i$ with Isobutanol/Toluene, pp. 416–420 (1984).

Stansfield et al., EMBO Journal, vol. 14, No. 17, "The products of the SUP45 (eRF1) and SUP35 genes interact to mediate translation termination in *Saccharomyces cerevisiae*", pp. 4365–4373 (1995).

Stone et al., Nucleic Acids Research, vol. 16, "The nucleotide sequence of the cDNA encoding the human lung protein phosphatase 2A–alpha catalytic subunit", p. 11365 (1988).

Strubin et al., Cell, vol. 80, "OBF–1, a Novel B Cell–Specific Coactivator That Stimulates Immunoglobulin Promoter Activity through Association with Octamer–Binding Proteins", pp. 497–506, Feb. 10, 1995.

Tassan et al., Molecular and Cellular Biology, vol. 13, No. 5, "In *Xenopupus laivis*, the Product of a Developmentally Regulated mRNA Is Structurally and Functionally Homologous to a *Saccharomyces cerevisiae* Protein Involved in Translation Fidelity", pp. 2815–2821 (1993).

Tate et al., "Termination of protein synthesis", Ribosomes and Protein Synthesis, A Practical Approach, Spedding, G/ed., IRL Press at Oxford, University Press, pp. 81–100 (1990).

Tuite et al. Nature, vol. 372, "Knowing when to stop", pp. 614–615 (1994).

Tung et al., Eur. J. Biochem, vol. 148, "The protein phosphatases involved in cellular regulation", pp. 253–263 (1985).

Turowski et al., The Journal of Cell Biology, vol. 129, No. 2, "Differential Methylation and Altered Conformation of Cytoplasmic and Nuclear Forms of Protein Phosphatase 2A During Cell Cycle Progression", pp. 397–410 (1995).

Waelkens et al., The Journal of Biological Chemistry, vol. 262, No. 3, "Purification and Properties of Polycation–stimulated Phosphorylase Phosphatases from Rabbit Skeletal Muscle", pp. 1049–1059 (1987).

Zhouravleva et al., The EMBO Journal, vol. 14, No. 16, "Termination of translation in eukaryotes is governed by two interacting polypeptide chain release factors, eRF1 and eRF3", pp. 4065–4072 (1995).

Zolnierowicz et al., Biochemistry, vol. 33, "Diversity in the Regulatory B–Subunits of Protein Phosphatase 2A: Identification of a Novel Isoform Highly Expressed in Brain", pp. 11858–11867 (1994).

Excerpts of PIR Nucleotide Sequence Data base, Ac. No. Pirl: Pahu2a and SO1986; A37235; A32143.

Cooke et al., The Plant Journal, vol. 9(1), "Further progress towards a catalogue of all Arabidopsis genes: analysis of a set of 5000 non–redundant ESTs", pp. 101–124 (1996).

Andjelković, Nataša—Inaugural Dissertation: "Structure, Regulation and Targeting of Protein Phosphatase 2A", May 15, 1998—Abstract.

Andjelković Nataša et al., NATO ASI Series (L. Heilmeyer, Editor), vol. H 102, "Interacting Protein Domains: Their Role in Signal and Energy Transduction", pp. 195–206 (1997).

SEQUENCE LISTING

<160> NUMBER OF SEQ ID NOS: 15

<210> SEQ ID NO 1
<211> LENGTH: 50
<212> TYPE: PRT
<213> ORGANISM: Rabbit
<220> FEATURE:
<221> NAME/KEY: PEPTIDE
<222> LOCATION: (1)..(50)
<223> OTHER INFORMATION: Binding site of PP2Ac for eRF1

<400> SEQUENCE: 1

Met Asp Glu Lys Val Phe Thr Lys Glu Leu Asp Gln Trp Ile Glu Gln
 1               5                  10                  15

Leu Asn Glu Cys Lys Gln Leu Ser Glu Ser Gln Val Lys Ser Leu Cys
            20                  25                  30

Glu Lys Ala Lys Glu Ile Leu Thr Lys Glu Ser Asn Val Gln Glu Val
        35                  40                  45

Arg Cys
    50

<210> SEQ ID NO 2
<211> LENGTH: 44
<212> TYPE: PRT
<213> ORGANISM: Homo sapiens
<220> FEATURE:
<221> NAME/KEY: PEPTIDE

```
<222> LOCATION: (1)..(44)
<223> OTHER INFORMATION: Binding site of ERF1 for PP2Ac

<400> SEQUENCE: 2

Thr Glu Glu Glu Lys Ile Leu Tyr Leu Thr Pro Glu Gln Glu Lys Asp
 1               5                  10                  15

Lys Ser His Phe Thr Asp Lys Glu Thr Gly Gln Glu His Glu Leu Ile
            20                  25                  30

Glu Ser Met Pro Leu Leu Glu Trp Phe Ala Asn Asn
        35                  40

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: tryptic
      peptide

<400> SEQUENCE: 3

Tyr Phe Asp Glu Ile Ser Gln Asp Thr Gly Leu
 1               5                  10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: tryptic
      peptide

<400> SEQUENCE: 4

Ile Leu Tyr Leu Thr Pro Glu Gln Glu Leu
 1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: tryptic
      peptide
<220> FEATURE:
<223> OTHER INFORMATION: x at position 1 is either Ser or Gly

<400> SEQUENCE: 5

Xaa Phe Gly Gly Ile Gly Gly Ile Leu
 1               5

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: degenerate
      oligonucleotide.  Modified base "i" at position 23

<400> SEQUENCE: 6
acaagcttta yttygaygar atnwscarga                                      30

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: peptide
      encoded by SEQ ID NO:6
```

```
<400> SEQUENCE: 7

Tyr Phe Asp Glu Ile Ser Gln Asp
 1               5

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: degenerate
      oligonucleotide
<220> FEATURE:
<223> OTHER INFORMATION: Modified base "i" at positions 20, 23 and 26.

<400> SEQUENCE: 8
acaagctttt ytcytgytcn ggngtnarrt a                              31

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: peptide
      encoded by SEQ ID NO :8

<400> SEQUENCE: 9

Tyr Leu Thr Pro Glu Gln Glu Leu
 1               5

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ataagcttca ccatggaact ttcagaacct                                30

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
tatggatcct tagtctttct ctggaacg                                  28

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
acgaattcat ggcggacgac cccagt                                    26

<210> SEQ ID NO 13
<211> LENGTH: 24
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 13
actctagact agtagtcatc aagg                                          24

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: peptide

<400> SEQUENCE: 14

Tyr Gln Gly Gly Asp Asp Glu Phe Phe Asp Leu Asp Asp Tyr
 1               5                  10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: peptide

<400> SEQUENCE: 15

Leu Arg Arg Ala Ser Val Ala
 1               5
```

PHOSPHATASE MODULATOR

The present invention relates to a modulator of protein phosphatase 2A (PP2A). In particular, the invention relates to the involvement of eRF1 in PP2A regulation and the use of modulators of the eRF1-PP2A interaction for the regulation of intracellular signalling and protein synthesis.

Protein phosphatase 2A (PP2A) is implicated in the regulation of many cellular processes including metabolism, signal transduction, growth, development, cell cycle progression and transformation (reviewed in Mumby, M. C. and Walter, G. (1993) *Physiol. Rev,* 73, 673–699; Mayer-Jaekel, R. E. and Hemmings, B. A. (1994) *Trends Cell Biol.,* 4, 287–291). PP2A is a family of trimeric holoenzymes which consist of a 36-kDa catalytic subunit (PP2Ac) bound to the constant regulatory subunit of 65 kDa (PR65/A) which then further associate with the third, variable regulatory subunit. Several trimeric PP2A holoenzymes have been purified which contain different variable subunits of either 54, 55, 72 or 74 kDa.

As documented by in vitro reconstitution assays and by analysing yeast and Drosophila mutants deficient in regulatory proteins, both constant and variable subunits are important for controlling PP2A activity and substrate specificity. For instance, PP2A activity from brain extracts of Drosophila aar$^r$ mutants, in which the gene encoding PR55 has been disrupted by P-element insertion, is several fold lower towards histone H1 and caldesmon phosphorylated by p342$^{cdc2}$ as compared to wild type flies. In contrast, phosphorylase phosphatase activity of PP2A is similar in aar$^1$ and control flies. The variable regulatory subunits also represent targets for potential second messengers and viral proteins. It has been demonstrated that ceramide activates only trimeric PP2A containing the PR55 subunit whereas the PP2Ac-PR65 dimer is unaffected. Recent data, however, show that neither the constant nor variable regulatory subunits are required for ceramide stimulation of PP2A activity, since both PP2Ac and PP2Ac-PR65 dimer could be stimulated by ceramide in a manner similar to that of the trimeric holoenzyme, suggesting that PP2Ac itself is a target of ceramide action. Furthermore, PP2A has also been shown to associate with transforming antigens of certain DNA tumour viruses, such as polyomavirus small t and middle T and SV40 small t. It is believed that these oncoproteins act to alter PP2A activity by displacing the normal cellular variable regulatory subunits from the trimeric holoenzyme. Some viral proteins interact only with specific forms of PP2A holoenzymes, e.g. SV40 small t antigen is able to replace only the B subunit (PR55), but not the B' subunit from trimeric PP2A. It was also shown that adenovirus E4orf4 binds to the trimeric PP2A holoenzyme that contains PR55. Taken together, these examples illustrate that activity of PP2Ac is tightly controlled in vivo by regulatory proteins.

Many components of the eukaryotic translational apparatus are known to be phosphorylated and in some cases phosphorylation has been shown to control the rate of translation. Furthermore, elongation and termination factors that directly function in maintaining translational accuracy are phosphorylated. Phosphorylation levels are also implicated in the control of translational fidelity in *Schizosaccharomyces pombe* since the allosuppressor gene, sal3, is allelic to cdc25, which is now known to encode a dual specificity protein phosphatase. Other examples of the involvement of protein phosphatases in the maintaining the accuracy of translation have been reported, most remarkable in this respect is the yeast translational allosuppressor SAL6, which has recently been identified as a serine/threonine protein phosphatase, termed PPQ.

A fundamental question in signal transduction is how protein kinases and protein phosphatases are regulated to phosphorylate/dephosphorylate the correct target proteins rapidly and preferentially at the correct time and place. The targeting hypothesis of Hubbard and Cohen, (1993) *Trends Biochem. Sci.,* 81, 172–177, postulates that a 'targeting subunit' directs protein kinases and phosphatases to specific subcellular locations where they act on their targets. A substantial amount of evidence exists to prove that several protein kinases and phosphatases with broad substrate specificity are recruited to their targets by specific interacting proteins. It was shown that the type 11 holoenzyme of the cAMP-dependent protein kinase (PKA) can be tethered to specific subcellular locations through the interaction of its regulatory (RII) subunit with A-kinase anchor proteins or AKAPs. Interestingly, PKA anchoring proteins were initially identified as proteins that co-purified with RII after affinity chromatography. Furthermore, a group of proteins termed RACKs (receptors for activated C-kinase) have been shown to bind to the activated form of the protein kinase C isoenzymes and mediate the translocation of the enzyme to the specific subcellular compartment where it exerts its action.

For PP2A, this type of regulation was thought to be mediated by its constituent regulatory subunits. But with regard to the numerous cellular processes in which PP2A is involved, it is feasible to speculate that a certain mode of regulation could also come from extrinsic proteins, rather than only from intrinsic holoenzyme components. The involvement of PP2A in disease related processes such as cell cycle progression and transformation implicates it and its control mechanism(s) as a target for therapy.

eRF1 is a polypeptide which modulates gene expression by influencing the release of polypeptide chains from the ribosome (Frolova et al., (1994) *Nature,* 372, 701–703). Members of eRF1 protein family have been identified from several higher eukaryotic organisms based on a significant sequence similarity to a ribosome-associated protein originally identified from the yeast *Saccharomyces cerevisiae* (Breining, P. and Piepersberg, W. (1986) *Nuc. Acid. Res.,* 14, 5098–5107). This protein, termed Sup45, has been implicated in maintaining translational fidelity through genetic analysis of mutants showing defective nonsense suppression in viva. Yeast Sup45 shows ~70% amino acid identity to its eukaryotic counterparts and a mutation in the SUP45 gene can be complemented by the *Xenopus laevis* Sup45 homologue Cl1, suggesting that its function in translation termination is a conserved evolutionary feature.

It was suggested that eRF1 was not the only release factor required for translation termination in vivo, since it had previously been shown that translational termination in eukaryotes is a GTP-dependent process, yet members of the eRF family do not contain any consensus GTP-binding sites themselves (Frolova et al., 1994). A likely candidate for this additional component of the eukaryotic translation termination machinery was proposed to be the Sup35 protein (Tuite, M. and Stansfield, I. (1994) *Nature,* 372, 614–615). Also originally described in *Saccharomyces cerevisiae,* mutants in the SUP35 gene show a similar array of phenotypes as SUP45mutants, suggesting the involvement of Sup35 in the process of translational termination (reviewed in Stansfield and Tuite, 1994) and it also contains several consensus GTP-binding sites.

Indeed, the most recent findings have shown that Sup45 (eRF1) and Sup35 (also termed eRF3) actually interact to form a release factor complex, both in yeast and higher eukaryotes (Zhouravleva, G. et al. (1995) *EMBO J.,* 14, 4065–4072; Stansfield, I. et al. (1995) *EMBO J.*, 14, 4365–4373). Sup35 (eRF3) is inactive as a release factor on its own but greatly stimulates the activity of eRF1, and one of its functions in the release factor complex could be GTP binding and hydrolysis. Reports that Sup35 is a prion-like protein which can exist in functionally different conformations suggest a possibility for the regulation of translational termination in eukaryotes.

A strategy for simultaneous purification of different PP2A holoenzymes from rabbit skeletal muscle has been developed in order to further analyse their subunit structure. This approach resulted in the purification of two heterotrimeric forms of $PP2A_0$ containing different isoforms of a novel type of variable regulatory subunit (termed PR61) that probably function to target PP2A to nuclear substrates. Furthermore, two novel proteins of 54 kDa and 55 kDa were found to co-purify with the trimeric $PP2A_1$ holoenzyme following affinity purification. The 54-kDa protein is eRF1.

SUMMARY OF THE INVENTION

The invention accordingly provides a method for identifying modulators of protein expression comprising screening for agents which affect the interaction between PP2A and eRF1. Moreover, the invention provides screening systems incorporating methods according to the invention and modulators of protein synthesis which target the eRF1-PP2A interaction.

DETAILED DESCRIPTION OF THE INVENTION

The invention is based on the elucidation of the interaction of the catalytic subunit of protein phosphatase 2A (PP2Ac) with the protein that belongs to a recently established protein family termed eRF1, which functions in the termination of protein synthesis as polypeptide chain release factor (Frolova et al., 1994). Identification of this protein was facilitated by the analysis of the subunit composition of purified PP2A preparations and co-purified proteins typically found in such preparations. The novelty of this result is that eRF1 is the first cellular protein other than the established regulatory subunits of PP2A so far found to interact with the catalytic subunit of PP2A. It also clarifies the mechanism whereby PP2A is involved in the regulation of protein synthesis. In view of the results which have lead to the present invention, eRF1 appears to play a dual role in (i) polypeptide chain termination, and (ii) recruitment of PP2A to the polysomes and, therefore, both eRF1 and PP2A provide a useful means for identifying modulators of protein expression which are capable of affecting the interaction between eRF1 and PP2A.

The method of the invention accordingly seeks to detect the interaction between eRF1 and PP2Ac, and to use this interaction to screen for compounds which are potential modulators of protein synthesis. The interaction between eRF1 and PP2Ac may be detected in a number of ways, with preferred detection methods including activation of reporter genes in genetic tests, the physical detection of protein binding in solution, such as by spectroscopic analysis, and solid phase binding assays wherein eRF1 and PP2Ac function as a co-operative binding pair, with detection being performed, for example, by means of enzyme/substrate reagents or the like, as is commonplace in assays such as ELISAs.

According to the invention, "eRF1" includes all polypeptides of the eRF1 family, as well as derivatives thereof which contain at least one common structural determinant. "Common structural determinant" means that the derivative in question has at least one structural feature of eRF1, consistent with that feature being involved in the binding of eRF1 and PP2Ac. Structural features includes possession of an epitope or antigenic site that is capable of cross-reacting with antibodies raised against a naturally occurring or denatured eRF1 polypeptide or fragment thereof, possession of amino acid sequence identity with eRF1 and features having common a structure/function relationship. Thus eRF1 as provided by the present invention includes splice variants encoded by mRNA generated by alternative splicing of a primary transcript, amino acid mutants, glycosylation variants and other covalent derivatives of eRF1 which retain the properties of eRF1 responsible for binding to PP2Ac. Exemplary derivatives include eRF1 molecules which are covalently modified by substitution, chemical, enzymatic, or other appropriate means with a moiety other than a naturally occurring amino acid. Such a moiety may be a detectable moiety such as an enzyme or a radioisotope. Further included are naturally occurring variants of eRF1 found with a particular species, preferably a mammal. Such a variant may be encoded by a related gene of the same gene family, by an allelic variant of a particular gene, or represent an alternative splicing variant of the eRF1 gene.

Derivatives which retain common structural features can be fragments of eRF1. Fragments of eRF1 comprise individual domains thereof, as well as smaller polypeptides derived from the domains. Preferably, smaller polypeptides derived from eRFl according to the invention define a single feature which is characteristic of eRF1. Fragments may in theory be almost any size, as long as they retain one feature of eRF1. Preferably, fragments will be between 5 and 200 amino acids in length. Longer fragments are regarded as truncations of the full-length eRF1 and generally encompassed by the term "eRF1".

Derivatives of eRF1 also comprise mutants thereof, which may contain amino acid deletions, additions or substitutions, subject to the requirement to maintain at least one feature characteristic of eRF1. Thus, conservative amino acid substitutions may be made substantially without altering the nature of eRF1, as may truncations from the 5' or 3' ends. Deletions and substitutions may moreover be made to the fragments of eRF1 comprised by the invention. eRF1 mutants may be produced from a DNA encoding eRF1 which has been subjected to in vitro mutagenesis resulting e.g. in an addition, exchange and/or deletion of one or more amino acids. For example, substitutional, deletional or insertional variants of eRF1 can be prepared by recombinant methods and screened for immuno-crossreactivity with the native forms of eRF1.

The fragments, mutants and other derivatives of eRF1 preferably retain substantial homology with eRF1. As used herein, "homology" means that the two entities share sufficient characteristics for the skilled person to determine that they are similar in origin and function. Preferably, homology is used to refer to sequence identity. Thus, the derivatives of eRF1 preferably retain substantial sequence identity with wild-type human eRF1 (Frolova et al., 1994).

"Substantial homology", where homology indicates sequence identity, means more than 50% sequence identity, preferably more than 75% sequence identity and most preferably a sequence identity of 90% or more.

As used herein, the terms PP2A and PP2Ac refer to protein phosphatase 2A and the catalytic subunit thereof, and should be interpreted as set forth above in respect of eRF1.

Since it has been found by deletion analysis, that the binding domains responsible for the interaction between PP2Ac and eRF1 are located within the 50 N-terminal amino acids of PP2Ac, and between amino acid residues 338 and 381 in the C-terminal part of human eRF1, preferred fragments, mutants and other derivatives of PP2Ac and eRF1 as defined above at least comprise these binding domains or functionally equivalent amino acid sequences.

A preferred method according to the invention is based on the two-hybrid system developed by Fields, S. and Song, O. (1989) Nature, 340, 345–346. According to this system, the DNA binding and transcriptional activation domains of a transcription factor are separated and complexed to two polypeptides whose cooperation it is sought to detect. If the potypeptides co-operate, the DNA binding and transcriptional activation domains are brought into association and the transcription factor is operative, which upregulates expression from a reporter gene. On the other hand, if the polypeptides do not co-operate, no active transcription factor is formed because the two domains thereof do not associate.

In this method, detection of upregulation of the reporter gene is dependent on successful cooperation between eRF1 and PP2Ac, so ultimate detection of binding is performed by assaying for reporter gene expression. Expression of visible markers, such as green fluorescent protein or β galactosidase, is preferred.

The interpretation of the method will depend on the nature of the compounds being screened. Thus, if screening for inhibitors, a lack of reporter gene expression comparative to a control is indicative of compound activity. Conversely, an increase in reporter gene expression comparative to control indicates that the compound may be active to potentiate eRF1/PP2Ac interaction. This pattern may be reversed by the use of DNA binding and/or transcription-influencing domains derived from a transcriptional silencer as opposed to a transcriptional activator.

The method of the invention may be applied to the design of screening systems to identify putative therapeutic agents for use in treating protein synthesis anomalies. Thus, the invention provides a method for screening potential modulators of intracellular signalling comprising the steps of:

(a) incubating eRF1 and PP2Ac or fragments thereof with the compound to be screened; and (b) detecting any modulation of the interaction between eRF1 and PP2Ac.

PP2Ac and eRF1 for use in the present invention may be in the form of isolated polypeptides or fragments thereof. As outlined above, preferred fragments of PP2Ac and eRF1 at least comprise their respective binding domains for eachother, i.e. the 50 N-terminal amino acids of PP2Ac (SEQ ID No. 1) and the amino acid residues 338 to 381 in the C-terminal part of human eRF1 (SEQ ID No. 2), or functionally equivalent fragments thereof capable of binding to eachother. Furthermore, PP2Ac and eRF1 may be in the form of the polypeptides or fragments complexed with further polypeptides. For example, in the case of a two-hybrid system-based screen, the polypeptide or fragment is complexed to a DNA binding or transcriptional activation domain derived from another protein, such as the yeast activator GAL4. The PP2Ac polypeptide or a fragment thereof is bound to either the transcriptional activator or the DNA binding element, while the eRF1 polypeptide or a fragment thereof is bound to the complementary domain.

Moreover, the method of the invention may be applied to the further elucidation of the mechanisms which control the activity of PP2A, by detecting and characterising cellular compounds which modulate the eRF1-PP2Ac interaction.

In a further aspect of the invention, there are provided compounds which modulate the interaction between eRF1 and PP2Ac. Such compounds may be potentiators of this interaction like eRF3, but preferably they are inhibitors thereof and act to impede binding between eRF1 and PP2Ac.

Candidate compounds include polypeptides derived from eRF1 or PP2Ac, which mimic the respective protein to the extent that they can compete therewith for binding to the other half of the binding pair, as well as anti-eRF1 and anti-PP2Ac antibodies which are capable of disrupting the binding of the two molecules. Preferred, however, are low molecular weight compounds which specifically inhibit binding and are suitable for pharmaceutical application. In a most preferred embodiment, candidate compounds are polypeptides having substantially the same physiological binding properties as provided by the 50 N-terminal amino acids of PP2Ac (SEQ ID No.1) and the amino acid residues 338 to 381 in the C-terminal part of human eRF1 (SEQ ID No. 2), or monoclonal antibodies specifically directed against these polypeptides.

Compounds according to the invention are candidate modulators of aberrant upregulation of protein synthesis and associated cellular proliferation, and accordingly may be useful for treating diseases associated with cellular proliferation, in particular cancer.

The invention is further described, for the purposes of illustration only, in the following examples.

Experimental

Co-purification of $PP2A_1$ holoenzvme with two proteins of 54- and 55-kDa

PP2A is purified from rabbit skeletal muscle using the protocol as modified by Zolnierowicz et al, (1994) Biochemistry, 33, 11858–11867. For the DEAE Sepharose chromatography step, the column (5×40 cm) is eluted with a 2000 ml gradient of 0.05 to 0.6 M NaCl. Fractions corresponding to PP2A eluting from DEAE Sepharose at 0.27–0.32 M, 0.34–0.38 M and 0.39–0.44 M NaCl (designated pool 1, pool 2 and pool 3, respectively) are combined and further purified. PP2A in pools 1 and 3 is purified by sequential chromatography on poly-L-lysine Agarose, ω-aminohexyl Sepharose and thiophosphorylase a-Sepharose columns. For PP2A in pool 2, the enzyme is purified by poly-L-lysine Agarose and thiophosphorylase a-Sepharose. The final purification step for all three PP2A preparations involves ion exchange MonoQ FPLC (0.5×5 cm column, Pharmacia) using a 40 ml gradient from 0.2 to 0.5 M NaCl. PP2A activity throughout purification is monitored by assaying protamine-stimulated phosphorylase phosphatase activity as described by Waelkens et al. (1987) J. Biol. Chem., 262, 1049–1059. The purified proteins obtained from the final steps are analysed by SDS-PAGE and immunodetection by Western blotting. The partially purified material obtained from DEAE-Sepharose pools 1, 2 and 3 are analysed using several antisera developed against the constituent subunits of PP2A reported in earlier publications (Hendrix et al., (1993a) J. Biol. Chem., 268, 15267–15276; Hendrix et al., (1993b) J. Biol. Chem., 268, 7330–7337; Turowski et al., (1995) J. Cell Biol, 129, 397–410). MonoQ FPLC of fractions corresponding to pool 1 (eluted from DEAE Sepharose between 0.27– 0.32 M NaCl) revealed the existence of a trimeric PP2A holoenzyme conteining 36 kDa catalytic (PP2Ac) and 65 kDa regulatory (PR65) subunits and a novel type of variable regulatory subunits with apparent molecular weight ranging from 56 to 61 kDa. This trimeric holoenzyme corresponds to $PP2A_0$ according to the classification established previously by Tung et al. (1985) *Eur. J. Biochem.,* 148, 253–263.

SDS-PAGE analysis of pool 2 (fractions eluted from DEAE-Sepharose between 0.34 and 0.38 M NaCl) after the thiophosphorylase a-Sepharose purification step reveals that this preparation contains the 36 kDa catalytic and 65 kDa regulatory subunits and several proteins in the range of 54–55 kDa. Further fractionation by MonoQ FPLC results in the separation of PP2A$_1$ (trimer containing the 55 kDa regulatory subunit, PR55) and PP2A2 (the dimeric form of the enzyme) from two proteins of 54 and 55 kDa. These two proteins appear to be unrelated to PR55 since they do not cross-react with anti-PR55 antibodies. Free PR55a is identified in this preparation by SDS-PAGE and immunoblot analysis (fractions 37 and 38). This suggests that the PP2A2 identified probably results from the dissociation of PR55, and possibly the 54 and 55 kDa proteins, from the complex. 54 kDa Drotein that co-purifies with PP2A$_1$ is a member of the eRF1 family of proteins with polypeptide chain release factor activity The 54 and 55 kDa proteins purified by MonoQ FPLC chromatography are used to obtain protein sequence data according to established procedures. Sequences of three tryptic peptides comprising 30 amino acids derived from the 54 kDa protein are obtained: peptide 3, YFDEISQDTGK, SEQ. ID NO: 3 peptide 9/10, ILYLTPEQEK, SEQ. ID NO: 4 and peptide 25/26, S/GFGGIGGIL SEQ ID NO: 5. Comparison of these sequences using the FASTA program reveals 76% homology to the predicted protein sequence encoded by the *Saccharomyces cerevisiae* SUP45 gene. cDNAs corresponding to this protein that co-purifies with PP2A1 are isolated using a reverse transcription/PCR approach, as follows:

Single-stranded cDNA is prepared from human breast carcinoma cell line T47D as described previously (Healy et al., (1991) *Mol. Cell. Biol.,* 11, 5767–5780). Two degenerate oligonucleotides containing a HindIII restriction site (underlined) are synthesised; sense 5'-ACMGCTTTAYTTYGAYGARATIWSC-ARGA-3'SEQ ID NO: 6, corresponding to amino acid sequence YFDE-ISQD SEQ ID NO: 7 and antisense 5'-ACAAGCTTTTYTCYTGYTCIGGIGTIARRTA-3' SEQ ID NO: 8, corresponding to amino acids YLTPEQEK SEQ ID NO: 9. PCR is performed using AmpliTaq DNA polymerase (Perkin Elmer). PCR products are gel-purified as described in Sambrook et al. (1989) *Molecular cloning: A Laboratory Manual,* Cold Spring Harbor Laboratory, Cold Spring Harbor, N.Y., subcloned into the HindIII site of pBluescript (Stratagene) and sequenced using Sequenase 2.0 (USB). PCR clone 18 contains an insert of 188 bp encoding a 62 amino acid-polypeptide with 57% identity to the yeast SUP45 gene product and is subsequently used for screening human fetal brain cDNA library (Stratagene). DNA is labelled with [$\alpha$-$^{32}$P]dATP by the random priming method of Feinberg and Vogelstein (1983) *Anal. Biochem.,* 132, 6–13, to a specific activity of approximately $10^9$cpm/$\mu$g. cDNA library screening is carried out as previously described (Hendrix et al., 1993a). A cDNA encoding human eRF3 is amplified from reverse-transcribed T47D total cDNA which is prepared as described above using the following PCR oligonucleotides: sense 5'ATAAGCTTCAC-CATGGAACTTTCAGMCCT 3' SEQ ID NO: 10 (HindIII site is underlined) and antisense 5'TATGGATCCT-TAGTCTTTTCTCTGGMCG 3' SEQ ID NO: 11 (BamHI site is underlined). The PCR products are subloned in pBluescript and sequenced as described above.

Among several clones isolated from the human fetal brain library and analysed by sequencing, only one, termed BBZ.eRF1-4b, contains a full length open reading frame (1311 bp) as well as 231 bp of the 5'-noncoding region and approximately 2,22 kb of the 3'-noncoding region. This cDNA is identical to the TB3-1 cDNA (Frolova et al., 1994). cDNAs encoding homologous proteins have also been identified in *Arabidopsis thaliana* (Quigley et al., The EMBL data bank, Release 37) and *Xenopus laevis* (Tassan et al, (1993) *Mol. Cell. Biol.,* 13, 2815–2821). The protein encoded by this cDNA is eRF1. A sequence comparison reveals that eRF1 protein is highly conserved between species, with yeast and human protein being 67.5% identical.

mRNA encoding human eRF1 is ubiquitously expressed

The levels of transcripts encoding human eRF1 are analysed in poly(A)$^+$ RNA isolated from different human tissues. With the probe corresponding to the complete human eRF1 cDNA (BBZ.eRF1-4b) labelled by random priming multiple transcripts are detected of approximately 2, 2.5 and 4 kb by northern blotting according to established procedures. mRNA encoding human eRF1 appears to be ubiquitously expressed, with the highest transcript levels found in lung, skeletal muscle and placental tissues. Of the three classes of transcripts detected, the 4-kb species shows the highest level of expression in all tissues. Quantitation by ImageQant software shows that 2.5 and 2 kb classes of transcripts are expressed approximately 2 to 4-fold less than the high molecular weight transcript. This mRNA distribution is different to that reported for Cl1, *Xenopus laevise* RF1 homologue, where a much more restricted pattern of expression was found, with both mRNA and the protein being completely absent in liver (Tassan et al., 1993).

Human eRF1 specifically interacts with the catalytic subunit of PP2A in the yeast two-hybrid system In order to assess which subunit of PP2A associates with human eRF1 and whether eRF3 which has been shown to bind to eRF1 and stimulate its activity in polypeptide chain termination in *S. cerevisiae* and *X. laevis* can be an interaction partner as well, the yeast two-hybrid system (Fields and Song, 1989) is employed using the Matchmaker™ Two-Hybrid System (Clontech Laboratories, Inc.). The cDNAs encoding full length human PP2Ac$\alpha$ (Khew-Goodall et al, (1991) *Biochemistry* 30, 89–97), PR65a (Hemmings et al., (1990) *Biochemistry,* 29, 3166–3173), PR55a (Mayer et at, (1991) *Biochemistry,* 30, 3589–3597), eRF1 and eRF3 are fused in-frame with the GAL4 DNA binding and/or trans-activation domains using pGBT9 and pGAD424 expression vectors, respectively. A series of N- and C-terminal deletions are constructed for both PP2Ac and eRF1 using a PCR-based strategy. PCR products encoding three N-terminal (eRF1$^{51-437}$, eRF1$^{93-437}$ and eRF1$^{150-437}$) and three C-terminal truncations (eRF1$^{1-411}$, eRF1$^{1-381}$ and eRF1$^{1-338}$) of human eRF1 are subcloned into pGAD424 in-frame with the GAL4 transactivation domain. PCR products encoding three N-terminal (PP2Ac$^{50-309}$, PP2Ac$^{100-309}$ and PP2Ac$^{150-309}$) and three C-terminal (PP2Ac$^{1-259}$, PP2Ac$^{1-209}$ and PP2Ac$^{1-159}$) truncations of PP2Ac$\alpha$ are subcloned into pGBT9 in-frame with the GAL4 DNA binding domain. Control plasmids encoding wild-type GAL4 protein (pCL1), SV40 large T antigen (pTD1), p53 (pVA3) and lamin C (pLAM5'), the latter three fused to the appropriate domains of GAL4, are provided by the manufacturer and used for control interactions. Expression constructs are transformed into *S. cerevisiae* host strains SFY526 (lacZ reporter gene) and HF7c (lacZ and HIS3 reporter genes). The expression of fusion proteins is checked in double transformants selected for growth on selective SD medium lacking leucine and tryptophan, and the interaction of PP2A subunits with human eRF1 and eRF3 evaluated by monitoring the expression of two different reporter genes, lacZ and HIS3. The expression of the lacZreporter gene is determined by measuring β-galactosidase activity using 5-bromo-4-chloro-3-indolyl-β-D-galactoside [X-Gal] and O-nitrophenyl-β-D-galactoside [ONPG] as substrates, whereas the expression of HIS3 reporter gene is assessed by monitoring growth on triple selective SD medium lacking leucine, tryptophan and histidine. All media and reagents are prepared according to the manufacturer's recommendations. Transcriptional activation of reporter genes driven by wild-type GAL4 protein or brought about by the interaction between SV40 largeT and p53 are used as positive controls. To exclude intrinsic transcriptional activation capacity or non-specific binding of either molecules to unrelated proteins, cotransformations with the empty vector or vector encoding human lamin C fused to the opposite domain of GAL4 are used as negative controls.

These experiments show that human eRF1 binds to eRF3 and that it directly and specifically interacts with PP2Ac, but not with PR65 or PR55, in both reporter systems, since only PP2Ac/eRF1 double transformants are β-galactosidase positive as confirmed by filter β-galactosidase assays (Table I) and do not require histidine for growth. From this analysis it follows that the PP2A subunit that binds eRF1 is the catalytic subunit itself. On the other hand, eRF3 interestingly fails to bind to either of the three PP2A subunits tested in this system.

Identification of domains required for the interaction of PP2Ac and eRF1

In addition to the analysis of interactions of full-length proteins in the two-hybrid system, the regions on both eRF1 and PP2Ac required for this association are mapped. For this purpose, a series of N- and C-terminally truncated versions of both proteins is constructed and tested in the same experimental set-up as described above. All of the three C-terminal deletion mutants of PP2Ac (PP2Ac$^{1-259}$, PP2Ac$^{1-209}$ and PP2Ac$^{1-159}$), but none of the N-terminal deletion mutants (PP2Ac$^{50-309}$, PP2Ac$^{100-309}$ and PP2Ac$^{150-309}$) are able to interact with eRF1. Accordingly, the region of PP2Ac required for binding to eRF1 is located within the N-terminal 50 amino acid residues of the protein. Differences in binding of the C-terminal truncations of PP2Ac to the full-length eRF1 suggests that the C-terminal portion of the protein also contains sequences that influence this interaction. N-terminal deletion mutants of eRF1 (eRF1$^{51-437}$, eRF1$^{93-437}$ and eRF1$^{150-437}$) still retain this interaction and, of the three C-terminal deletions of eRF1 (eRF1$^{1-411}$, eRF1$^{1-381}$ and eRF1$^{1-338}$), only the largest one, truncating the protein at Thr$^{338}$, fails to bind to PP2Ac. This indicates that the putative binding domain on eRF1 lies between Thr$^{338}$ and Asn$^{381}$. However, even the minimally sufficient polypeptides defined from these experiments (PP2Ac$^{1-159}$ and eRF1$^{1-381}$) are still able to interact with each other, although in a comparably faint manner. A summary of all interactions tested in the two-hybrid system is presented in Table I.

TABLE I

Summary of all interactions tested in the two-hybrid analysis of PP2A/eRF1 association.

| Double transformants | His growth (HF7c) | Colony colour in filter β-Gal assays (SFY526) |
|---|---|---|
| pCL1/pLAM5' (wtGAL4) | + | blue |
| pTD1/pVA3 (SV40 largeT/p53) | + | blue |
| pGBT9.PP2Acα/pGAD424. eRF1 | + | blue |
| pGBT9.PR65α/pGAD424. eRF1 | − | white |
| pGBT9.PR55α/pGAD424. eRF1 | − | white |
| pGBT9/pGAD424. eRF1 | − | white |
| pGBT9.PP2Acα/pGAD424 | − | white |
| pGBT9.PR65α/pGAD424 | − | white |
| pGBT9.PR55α/pGAD424 | − | white |
| pGBT9/eRF1$^{51-437}$ | − | white |
| pGBT9/eRF1$^{93-437}$ | − | white |
| pGBT9/eRF1$^{150-437}$ | − | white |
| pGBT9/eRF1$^{1-411}$ | − | white |
| pGBT9/eRF1$^{1-381}$ | − | white |
| pGBT9/eRF1$^{1-338}$ | − | white |
| pGBT9.PP2Ac/eRF1$^{51-437}$ | + | blue |
| pGBT9.PP2Ac/eRF1$^{93-437}$ | + | blue |
| pGBT9.PP2Ac/eRF1$^{150-437}$ | + | blue |
| pGBT9.PP2Ac/eRF1$^{1-411}$ | + | blue |
| pGBT9.PP2Ac/eRF1$^{1-381}$ | + | blue |
| pGBT9.PP2Ac/eRF1$^{1-338}$ | − | white |
| PP2Ac$^{50-309}$/pGAD424 | − | white |
| PP2Ac$^{100-309}$/pGAD424 | − | white |
| PP2Ac$^{150-309}$/pGAD424 | − | white |
| PP2Ac$^{1-259}$/pGAD424 | − | white |
| PP2Ac$^{1-209}$/pGAD424 | − | white |
| PP2Ac$^{1-159}$/pGAD424 | − | white |
| PP2Ac$^{50-309}$/pGAD424.eRF1 | − | white |
| PP2Ac$^{100-309}$/pGAD424.eRF1 | − | white |
| PP2Ac$^{150-309}$/pGAD424.eRF1 | − | white |
| PP2Ac$^{1-259}$/pGAD424.eRF1 | + | blue |
| PP2Ac$^{1-209}$/pGAD424.eRF1 | + | blue |
| PP2Ac$^{1-159}$/pGAD424.eRF1 | + | blue |

Immunoprecipitates of eRF1 contain PP2A activity

To test whether complex formation between PP2A and eRF1 occurs in mammalian cells, it is determined whether these two proteins co-immunoprecipitate. Association between PP2Ac and PR65 under the same experimental conditions is used as a positive control. For transient expression in COS-1 cells, human eRF1, eRF3 and PR65α are tagged with the hemagglutinin (HA)-epitope at the respective N-terminus. PCR is used to introduce an EcoRI site at the 5' end and an XbaI site at the 3' end of the coding region of the human eRF1 cDNA using the following oligonucleotides: sense 5'-ACGMTTCATGGCGGACGACCCCAGT-3' SEQ ID NO: 12 and antisense 5'-ACTCTAGACTAGTAGTCATCAAGG-3'SEQ ID NO: 13. The EcoRI-XbaI fragment is subcloned into mammalian expression vector pEV3S (Strubin, M. et al. (1995) *Cell*, 80, 497–506) to add the HA tag to the N-terminus of the protein. A HindII—BamH fragment encoding human eRF3 is passed through the pMV vector to add the HA tag to the N-terminus of the protein, and subsequently subcloned into pECE eukaryotic expression vector as a KpnI—Sad fragment. A pRC/CMV expression construct encoding HA-tagged human PR65α is similarly constructed.

The cells are transfected by the DEAE-dextran method and collected 48–60 hours after transfection in 1× TBS (150 mM NaCl, 50 mM Tris-HCl pH 7.4). Whole cells are lysed by 20 strokes in a Dounce homogeniser in 1× TBS containing 0.1% 2-mercaptoethanol, 0.5 mM EDTA, 1 mM phenylmethylsulfonyl fluoride, 1 mM benzamidine-HCl, 0.1 mM N'-tosyl-L-lysine chloromethylketone-HCl, 0.1 mM tosyl-L-phenylalanine chloromethylketone, 2 μg/ml leupeptin, 2

μg/ml aprotinin and 2 μg/ml pepstatin A. The homogenates are centrifuged at 4° C. for 15 min at 10,000× g. Protein determinations are carried out using the Bio-Rad Bradford reagent according to the manufacturer's instructions with bovine serum albumin as protein standard.

Freshly prepared COS-1 cell extracts are precleared twice with 1/20 volume Pansorbin (Calbiochem). Protein A Sepharose (Pharmacia Biotech Inc.) washed three times with lysis buffer, is incubated with 12CA5 monoclonal antibody specific for the HA tag overnight at 4° C. and then washed extensively with lysis buffer to remove excess antibody. Precleared extracts are added to the constant amount of antibody-saturated protein A Sepharose and incubated for 4 hours at 4° C. with mixing. Pelleted beads are washed three times in lysis buffer and resuspended in 1× SDS sample buffer for SDS-PAGE analysis or assay buffer for phosphatase activity measurements (Shacter, E. (1984) *Anal. Biochem.*, 138, 416–420).

Preparation of peptide-specific antisera and Western blot analysis

Antisera are prepared to human eRF1 by immunization with a peptide YQGGDDEFFDLDDY SEQ ID NO: 14 (amino acids 424–437) corresponding to the C-terminus of the protein. Peptide synthesis and coupling to keyhole limpet hemocyanin with glutaraldehyde and subsequent immunization of rabbits as well as protein transfer and Western blot analysis are carried out as described by Hendrix et al. (1993b). Antibodies used to detect PP2A subunits in purified holoenzymes are peptide-specific rabbit polyclonal antisera: Ab $C^{1-20}$ (against the N-terminal peptide of PP2Ac), Ab $65^{177-196}$ (against the internal peptide of PR65, Turowski et al., 1995), Ab $55\alpha^{1-19}$ (against the N-terminal peptide of PR55α, Hendrix et al., 1993b), and Ab $72/130^{COOH}$ (against the C-terminal peptide of PR72/130, Hendrix et al., 1993a). Antibodies used to detect specific proteins in immunoprecipitates are: Ab eRF1$^{424-437}$ (against the C-terminal peptide of human eRF1), Ab $C^{1-20}$ and Ab 177-196, as well as 12CA5 monoclonal antibody specific to the HA-tag. For Ab eRF1$^{424-437}$ and 12CA5, IgG fractions are purified on Protein A/Sepharose beads (Pharmacia) as described by Harlow and Lane (1988) *Antibodies: A laboratory manual*. Cold Spring Harbor Laboratory Press, CSH, NY, and the other antibodies are used as crude antisera. Immunodetection is performed using $^{125}$I-conjugated donkey anti-rabbit IgGs (Amersham Corp.) for autoradiography. Primary antibodies are diluted 1:100 and secondary antibodies 1:1000 in blocking buffer. The blots are exposed for 12–24 hours in the Phosphorimager and quantified using ImageQuant software (Molecular Dynamics).

Extracts from COS-1 cells transiently transfected with human eRF1, eRF3 or PR65 tagged with the hemagglutinin (HA) epitope at the N-termini, as well as from mock transfected cells are subjected to immunoprecipitation with the anti-HA-tag monoclonal antibody 12CA5. PP2A activity is measured in transfected COS-1 cell extracts and the immunoprecipitates using a $^{32}$P-labeled peptide (LRRASVA Val$^6$, Ala$^7$SEQ ID NO: 15) as a substrate. Assays are performed in the presence and absence of 10 nM okadaic acid, which is used typically to distinguish between PP1 and PP2A activities. The results of these experiments show that the specific activity of PP2A in the extracts is in the same range for all transfected cells and that 12CA5 immunoprecipitates from cells transfected with HA-tagged eRF1 or PR65 contain significant okadaic acid-sensitive, PP2A-like phosphatase activity as compared with immunoprecipitates from mock-transfected cells (Table II). The amount of total cytoplasmic PP2A activity associated with eRF1 is also quantified. Immunoprecipitation of eRF1 brings down approximately 1% (0.4–1.6% range) of the total cytoplasmic PP2A activity, while the activity in PR65-immunoprecipitates is approximately 10-fold higher (Table II). Immunoprecipitation of eRF3 does not bring down PP2A activity significantly higher than the background. This result suggests that the interaction of PP2A and eRF3 with eRF1 are mutually exclusive.

TABLE II

Immunoprecipitation of eRF1 brings down PP2A activity.

|  | Extracts (mU) | Immunoprecipitates (mU) | % immunoprecipitated |
| --- | --- | --- | --- |
| HA-eRF1 transfected | 494 ± 26.7 | 1.9 ± 0.04 | 0.39 ± 0.01 |
| HA-PR65α transfected | 466 ± 25.2 | 17 ± 0.93 | 3.7 ± 0.20 |

PP2A activity is measured in extracts and 12CA5-immunoprecipitates from COS-1 cells transiently transfected with HA-tagged human eRF1, eRF3 or PR65α. PP2A activity is measured using $^{32}$P-labeled synthetic peptide (LRRASVA) as substrate in the presence and absence of 10 nM okadaic acid in duplicate assays. The numbers represent the mean values of three independent experiments ±SEM. Specific activity of the extracts (U/mg protein) is the same for mock transfected and HA-PR65/HA-eRF1/HA-eRF3 transfected cells (about 2.4 U/mg). In immunoprecipitates from mock transfected cells the value of phosphatase activity brought down by non-specific binding to protein A Sepharose is less than 0.1 mU.

PP2Ac and eRF1 are associated in vivo in mammalian cells

To determine which PP2A subunits are present in the complex with eRF1, HA-eRF1-immunoprecipitates are subjected to Western blotting with rabbit polyclonal anti-peptide antibodies specific for the following different subunits of PP2A: (Ab C-$^{1-20}$, Ab $65^{177-196}$, Ab $55\alpha^{1-19}$ and Ab $72/130^{COOH}$). These experiments reveal that PP2Ac can be detected in immunoprecipitates from HA-eRF1- or HA-PR65-transfected, but not from mock-transfected cells. When checking for the presence of other established regulatory subunits of PP2A in eRF1 immunoprecipitates, PR65 but not PR55 or PR72 are detected. It is thus concluded that eRF1 complexes with the core dimer of PP2A consisting of PP2Ac and PR65 to form a novel trimeric complex, which is much less abundant than other complexes of PP2A. These results provide the first evidence for an in vivo association between the PP2A catalytic subunit and eRF1 protein in mammalian cells.

Expression of HA-tagged eRF1 in COS-1 cells increases the amount of PP2A associated with the polysomes The distribution of PP2A in fractionated exponentially growing COS-1 cells, as well as in COS-1 cells transiently transfected with HA-tagged eRF1 is investigated. Ribosomes (80S) from these cells are obtained by high speed centrifugation of cell free extracts through a 38% sucrose cushion. Controls are performed using antibodies specific to ribosomal (S6) and cytosolic (regulatory RII subunit of protein kinase A) proteins to evaluate successful separation. PP2A distribution is analyzed in total cell free extracts, and in the sucrose and ribosomal fractions. The analysis is carried out by Western blotting and activity measurements using $^{32}$P-labeled peptide (Kemptide Val$^6$, Ala$^7$) as a substrate. These experiments show that in untransfected COS-1 cells, PP2A present in the polysomes is a very small portion of total cytoplasmic PP2A activity (1–2%), which is in agreement with estimates from previous studies performed using rabbit reticulocyte lysates. However, overexpression of eRF1 significantly increases the amount of PP2A present in the polysomes, suggesting that PP2A can be recruited to the polysomes by increasing the amount of free eRF1 available to bind to PP2Ac. The data from activity measurements are subsequently confirmed by Western blot analysis of PP2A and eRF1, that shows a significant increase of PP2Ac and PR65 in COS-1 cells following overexpression of eRF1. The slower migrating band cross-reacting with eRF1 antibody represents the HA-tagged form. In contrast to previous reports on S. cerevisiae homologue Sup45 (Stansfield et al., 1992), mammalian eRF1 is shown not to be exclusively present in the polysomal fraction, but rather equally distributed between cytoplasmic and polysomal fractions, which may point to its relatively loose attachement to the 40S subunit in mammalian cells.

Subsequent immunoprecipitation experiments from fractionated COS-1 cells described above, followed by activity measurements and immunoblotting, show that PP2A dimer and associated, okadaic acid sensitive phosphatase activity are present in immunoprecipitated fractions of eRF1, confirming that indeed increased PP2A detected in the polysome fraction is associated with eRF1.

Effects of different forms of PP2A on polypeptide chain release factor activity of eRF1

Since initially no effect of eRF1 has been observed on basal or protamine-stimulated activity of PP2A, possible effects of PP2A on polypeptide chain release factor activity of eRF1 are investigated. Accordingly, the stop codon-dependent release of f [$^{35}$S] methionine from the f [$^{35}$S] methionyl-tRNA$^{fMet}$-AUG-80S substrate complex mediated by eRF1 is measured in an in vitro termination assay (Tate, W. P. and Caskey, C. T. (1990) in Spedding, G. (ed.), *Ribosomes and Protein Synthesis. A Practical Approach*, IRL Press at Oxford University Press, 88–100). These experiments are performed using recombinant human histidine-tagged eRF1 (His-eRF1) and GST-tagged eRF3 (GST-eRF3) purified to apparent homogeneity, as well as purified preparations of PP2Ac, PP2A$_2$ and PP2A$_1$. His-eRF1 is active as a release factor on its own, but treatment with equimolar concentrations of different forms of PP2A does not have any dramatic effects on the activity of the recombinant protein. As previously reported for the S. cerevisiae and X. laevis homologues, GST-eRF3 is able to stimulate eRF1 release factor activity. There is no significant effetct of different PP2A preparations on eRF3-stimulated activity of His-eRF1. Furthermore, the release activity of a MonoQ purified preparation of PP2A that contains eRF1 (MQ I), as confirmed by Western blotting analysis with Ab eRF1$^{424-437}$ is tested. eRF1 present in this preparation is also active in termination assays, although to somewhat lower extent than the recombinant protein, but the activity in the presence of 10 nM okadaic acid (Sigma) is not significantly different to that in untreated samples.

To further understand the interaction of PP2A with eRF1, the release activity in immunoprecipitates of HA-eRF1 from transfected COS-1 cells is determined. The data indicate that the activity of eRF1 is extremely low (>5%) compared to the similar amount of recombinant protein. These immunoprecipitates contain PP2Ac and PR65. These results suggest at least two possibilities: (a) the eRF1-immunoprecipitates contain additional protein(s) that inhibit its activity (in this case partially purified eRF1 would be devoid of this putative inhibitory protein, hence explaining its activity), or (b) eRF1 immobilized on protein A Sepharose beads via 12CA5 monoclonal antibody is unable due to size restrictions to get access to the substrate on the ribosome.

Taken together these results indicate a complex relationship between eRF1 activity and association with PP2A and/or eRF3.

What is claimed is:

1. A method for identifying modulators of protein expression comprising the steps of:
   (a) incubating eRF1 and PP2Ac or fragments thereof with a candidate modulator;
   (b) comparing the binding of PP2Ac and eRF1 in the presence or absence of the modulator; and
   (c) detecting modulation of the interaction between eRF1 and PP2Ac
wherein PP2Ac comprises SEQ ID NO:1 and eRF1 comprises SEQ ID NO:2 and wherein the fragment of PP2Ac and the fragment of eRF1 can bind to each other.

2. A method according to claim 1, wherein the interaction between eRF1 and PP2Ac is detected using a genetic test.

3. A method according to claim 1, wherein the interaction between eRF1 and PP2Ac is detected using a solid phase binding assay.

4. A method according to claim 2, wherein detection is performed by assessing reporter gene expression.

* * * * *